(12) United States Patent
Archat et al.

(10) Patent No.: US 11,992,649 B2
(45) Date of Patent: May 28, 2024

(54) INFUSION DEVICE COMPRISING A PUMPING MECHANISM

(71) Applicant: Fresenius Vial SAS, Brézins (FR)

(72) Inventors: Damien Archat, Grénoble (FR); Mathieu Paoli, La Murette (FR)

(73) Assignee: Fresenius Vial SAS, Brézins (FR)

( * ) Notice: Subject to any disclaimer, the term of this patent is extended or adjusted under 35 U.S.C. 154(b) by 259 days.

(21) Appl. No.: 17/418,232

(22) PCT Filed: Dec. 13, 2019

(86) PCT No.: PCT/EP2019/085158
§ 371 (c)(1),
(2) Date: Jun. 24, 2021

(87) PCT Pub. No.: WO2020/160822
PCT Pub. Date: Aug. 13, 2020

(65) Prior Publication Data
US 2022/0062534 A1     Mar. 3, 2022

(30) Foreign Application Priority Data
Feb. 4, 2019 (EP) .................................... 19305130

(51) Int. Cl.
*A61M 5/142*         (2006.01)
(52) U.S. Cl.
CPC ... *A61M 5/14228* (2013.01); *A61M 2205/103* (2013.01)
(58) Field of Classification Search
CPC ................. A61M 5/14228; A61M 2205/103
See application file for complete search history.

(56) References Cited

U.S. PATENT DOCUMENTS

| 4,772,263 A | * | 9/1988 | Dorman | ............ A61M 5/14276 604/134 |
| 4,856,972 A | * | 8/1989 | Van Benschoten | ..... F04B 43/12 604/153 |

(Continued)

FOREIGN PATENT DOCUMENTS

| CN | 106061540 A | 10/2016 |
| CN | 109310817 A | 2/2019 |

(Continued)

OTHER PUBLICATIONS

International Search Report and Written Opinion, counterpart International Appl. No. PCT/EP2019/085158 (dated Jan. 30, 2020) (11 pages).

(Continued)

*Primary Examiner* — Bradley J Osinski
(74) *Attorney, Agent, or Firm* — Cook Alex Ltd.

(57) ABSTRACT

An infusion device (1) for administering a medical fluid to a patient (P) comprises a pumping mechanism (4) configured to act onto a fluid conduit (20), the pumping mechanism (4) comprising a pumping section (42) movable with respect to said fluid conduit (20) for causing a fluid flow (F) through said fluid conduit (20). The pumping mechanism (4) comprises a multiplicity of rotatable gear elements (45A-45E) coupled to the pumping section (42) at a multiplicity of different locations (43A-43E), wherein the gear elements (45A, 45E) are operatively coupled to each other for a coordinated rotation of the gear elements (45A-45E) for moving the pumping section (42). In this way an infusion device is provided which may allow for a small-sized pumping mechanism, yet providing for a reliable and efficient infusion operation.

13 Claims, 9 Drawing Sheets

(56) References Cited

U.S. PATENT DOCUMENTS

| | | |
|---|---|---|
| 2005/0240146 A1 | 10/2005 | Nash et al. |
| 2010/0143168 A1* | 6/2010 | Miyazaki .............. F04B 43/082 |
| | | 417/412 |
| 2012/0163999 A1 | 6/2012 | Becker |
| 2017/0049999 A1 | 2/2017 | Kim |
| 2018/0117243 A1 | 5/2018 | Maguire |
| 2019/0201617 A1 | 7/2019 | Weibel et al. |

FOREIGN PATENT DOCUMENTS

| | | |
|---|---|---|
| JP | H07-224764 | 8/1995 |
| WO | WO2010/088143 | 8/2010 |
| WO | WO2012/049263 | 4/2012 |
| WO | WO2013/023939 | 2/2013 |

OTHER PUBLICATIONS

Office Action and Search Report (with English-language translation), counterpart Chinese App. No. 201980091102 (dated Feb. 7, 2023) (18 pages).

\* cited by examiner

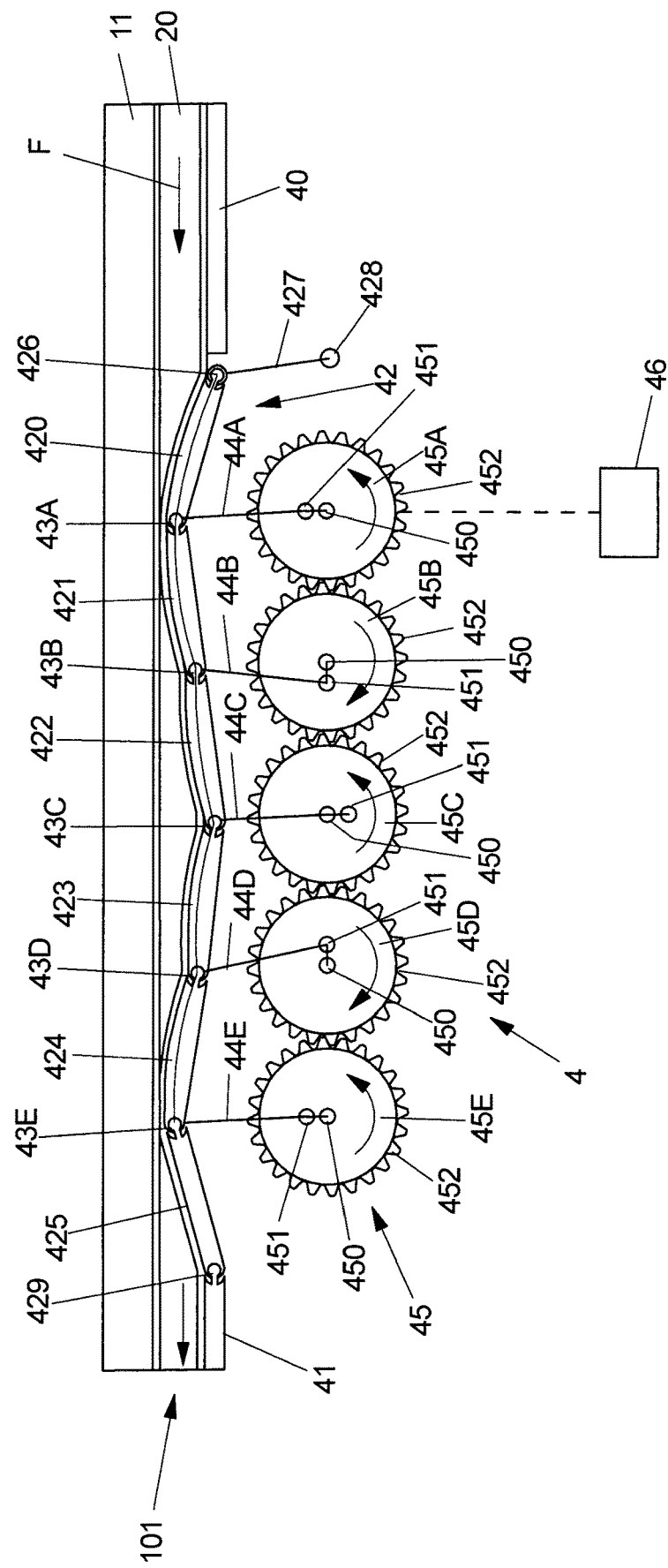

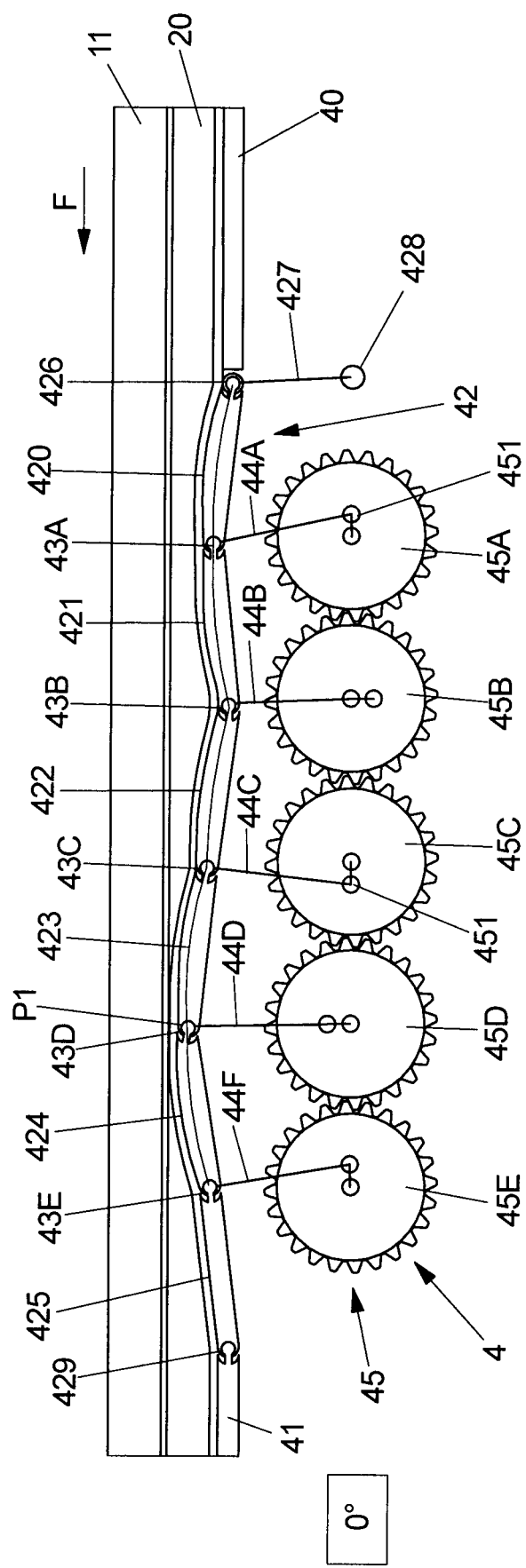

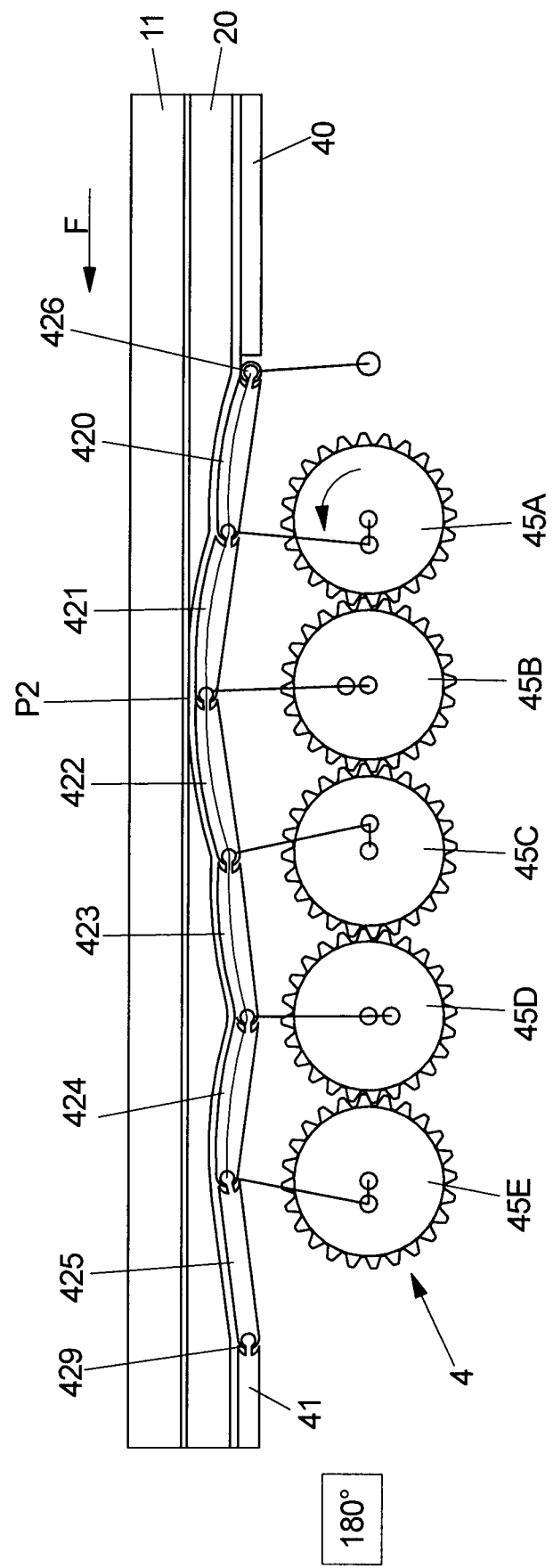

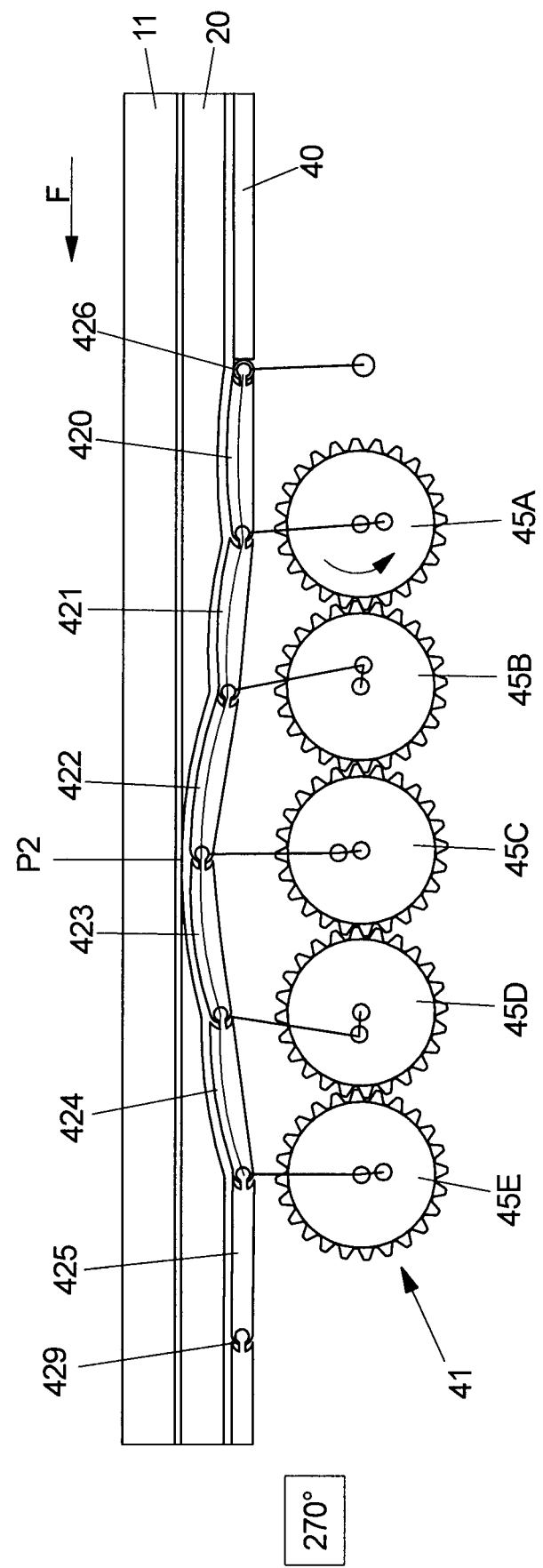

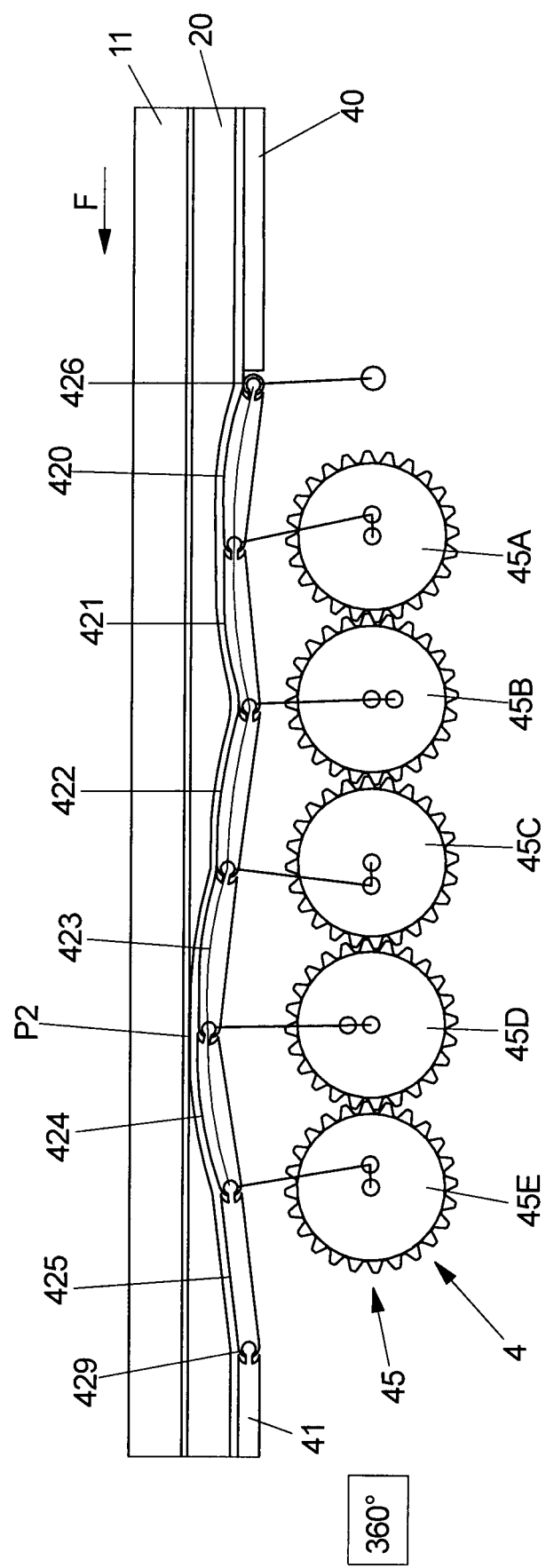

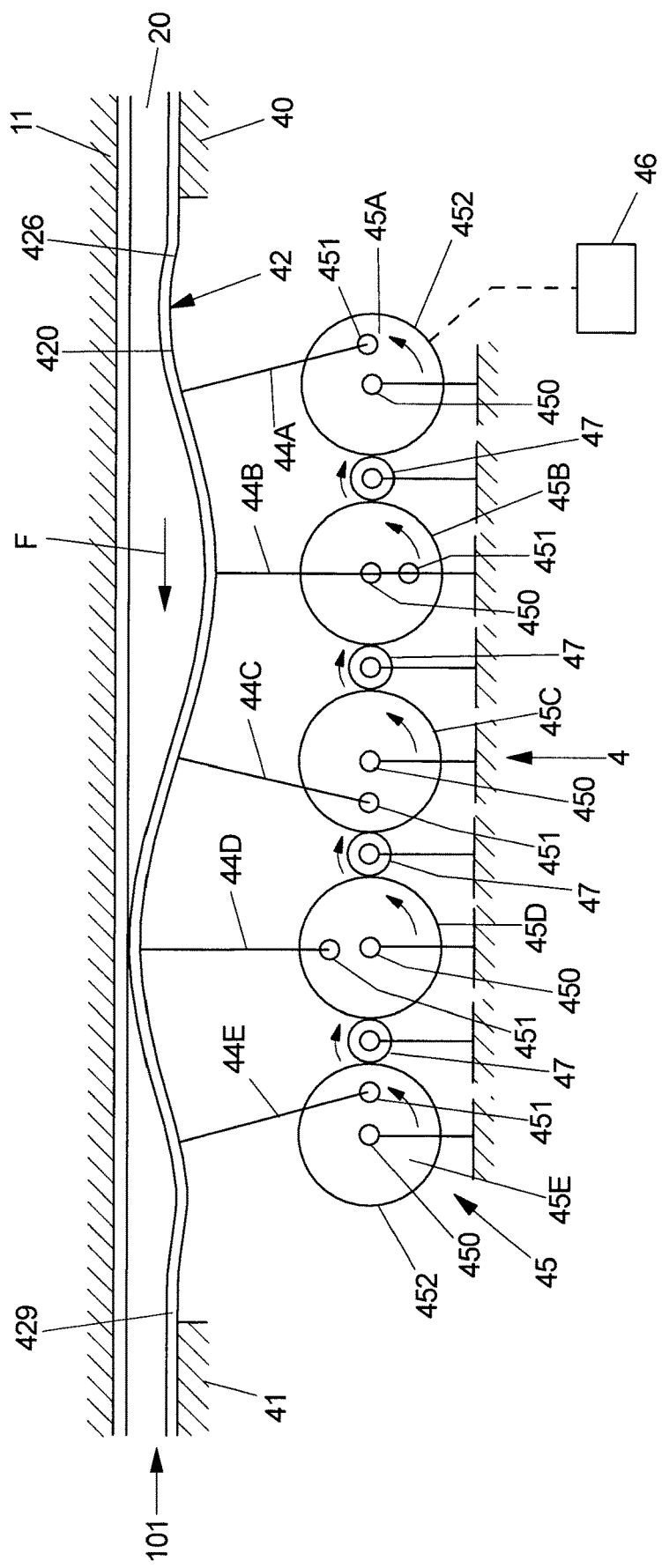

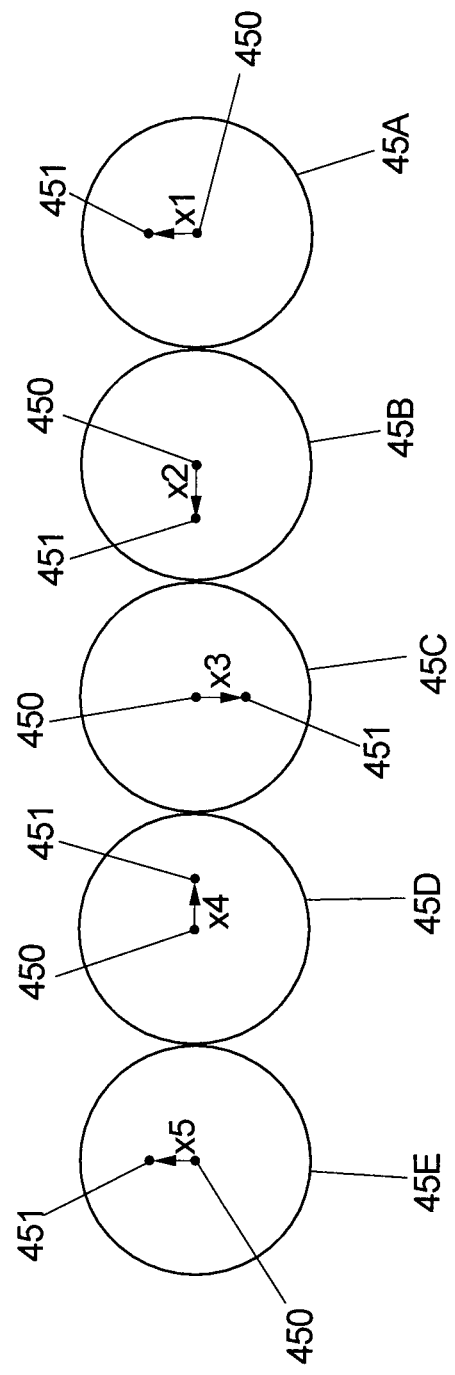

INFUSION DEVICE COMPRISING A PUMPING MECHANISM

The present application is a U.S. National Stage of PCT International Patent Application No. PCT/EP2019/085158, filed Dec. 13, 2019, which claims priority to EP Application No. 19305130.7, filed Feb. 4, 2019, both of which are hereby incorporated herein by reference.

The invention relates to an infusion device for administering a medical fluid to a patient according to the preamble of claim 1 and to a method for operating an infusion device.

An infusion device of this kind comprises a pumping mechanism configured to act onto a fluid conduit, the pumping mechanism comprising a pumping section movable with respect to said fluid conduit for causing a fluid flow through said fluid conduit.

An infusion device of this kind is generally denoted as a volumetric (peristaltic) infusion pump. The pumping mechanism herein in a peristaltic fashion acts onto a fluid conduit, for example an infusion line, for transporting a medical fluid through the fluid conduit in order to deliver the medical fluid towards a patient.

A peristaltic infusion device as commonly known in the prior art for example comprises a pumping mechanism having a multiplicity of pump fingers for sequentially acting onto a fluid conduit in order to force fluid in a specified pumping direction through the conduit. Other peristaltic infusion devices use for example a wobble device which performs a wobbling action for acting onto a pump module comprising a membrane, the wobbling action causing a fluid to flow through the pump module.

There is a general desire to provide a peristaltic infusion device which may comprise a pumping mechanism of small size and easy construction, yet providing for a reliable and efficient pumping action.

WO 2012/049263 A1 discloses an infusion device comprising a pumping mechanism having a wobble mechanism for acting onto a pump module. A wobbling disc herein is connected at a slanted angle to a rotational shaft such that by rotating the shaft the wobbling disk can be moved to act onto a membrane of the pump module.

From WO 2010/088143 A1 a peristaltic infusion device is known which comprises a pumping mechanism having roller elements being placed on a common carrier element, the roller elements being configured to act onto a fluid conduit by rotating the carrier element in order to transport fluid through the fluid conduit.

It is an object of the instant invention to provide an infusion device and a method for operating an infusion device which may allow for a small-sized pumping mechanism, yet providing for a reliable and efficient infusion operation.

This object is achieved by means of an infusion device comprising the features of claim 1.

Accordingly, the pumping mechanism comprises a multiplicity of rotatable gear elements coupled to the pumping section at a multiplicity of different locations, wherein the gear elements are operatively coupled to each other for a coordinated rotation of the gear elements for moving the pumping section.

The pumping mechanism hence is designed to act onto a pumping section by means of a multiplicity of rotatable gear elements. The gear elements are coupled to the pumping section such that by rotating the gear elements the pumping section is moved in order to cause a fluid flow through the fluid conduit in order to administer a medical fluid to a patient.

The gear elements herein are operatively coupled to each other and hence form a gear train which ensures a coordinated rotation of the gear elements. Hence, the gear elements are rotated together such that the gear elements cannot be rotated independently of each other. Rather, a rotation of one gear element goes along with a rotation of all other gear elements, the rotation of the gear elements taking place in a coordinated fashion such that each gear element is moved in a defined manner if the other gear elements are rotated.

The gear train formed by the gear elements may for example be driven by a single drive device, for example in the shape of an electric motor. For this, the drive device may act onto one of the gear elements, the rotation of the one gear element causing a rotation of all other gear elements in a defined, coordinated fashion.

The gear elements may be mechanically coupled to each other for example by a meshing engagement. Alternatively, an electronic coupling is conceivable by rotating the gear elements by separate drive devices, the driving however being coordinated such that the gear elements are rotated together in a coordinated fashion.

The gear elements beneficially each are coupled to the pumping section such that each gear element acts onto the pumping section. The gear elements may be aligned along a longitudinal flow direction along which the fluid conduit extends, pivot axes of the gear elements extending transverse to the longitudinal flow direction and being displaced with respect to each other along the longitudinal flow direction.

The gear elements herein may be coupled to the pumping section such that the gear elements act onto the pumping section at locations which are displaced with respect to the each other along the longitudinal flow direction such that by means of the gear elements a sequential, peristaltic movement of the pumping section is possible for transporting fluid through the fluid conduit.

In one embodiment, each of the gear elements comprises a toothing such that a meshing engagement with other gear elements may be established. The gear train may be formed by neighbouring gear elements directly meshing with each other. Alternatively, one or multiple additional tooth wheels may be arranged between neighbouring gear elements such that neighbouring gear elements are coupled to each other indirectly via tooth wheels placed therebetween.

In one embodiment, neighbouring gear elements of the multiplicity of gear elements are operatively coupled to each other such that the neighbouring gear elements are operative to rotate in opposite rotational directions. For this, neighbouring gear elements may for example be in direct meshing engagement, such that a rotation of one gear element causes a rotation of a neighbouring gear element in an opposite rotational direction. Neighbouring gear elements hence are rotated in an opposite fashion, a rotation of one gear element in a clockwise direction for example causing a rotation of a neighbouring gear element in a counterclockwise direction.

In another embodiment neighbouring gear elements of the multiplicity of gear elements are operatively coupled to each other such that the neighbouring gear elements are operative to rotate in equal rotational directions. In this case, between neighbouring gear elements an additional tooth wheel may be arranged such that the neighbouring gear elements are coupled to each other by means of the intermediary tooth wheel. In this case the neighbouring gear elements rotate in equal directions, the rotation of one gear element for example in the clockwise direction causing a rotation of a neighbouring gear element also in the clockwise direction.

Generally, one or multiple tools wheels may be arranged in between neighbouring gear elements, such that the neighbouring gear elements may be coupled to each other by means of one or multiple intermediary tooth wheels. The gear train hence is formed by the gear elements in connection with the tooth wheels, the gear elements herein being coupled to the pumping section such that a rotation of the gear elements causes a movement of the pumping section for transporting a fluid through the fluid conduit.

In one embodiment, the pumping mechanism comprises a multiplicity of connecting elements connecting the gear elements to the pumping section, each connecting element being connected to the pumping section at one of the multiplicity of different locations. The gear elements hence are coupled to the pumping section by means of different connecting elements, for example having the shape of rods, such that a rotational movement of the gear elements is transferred to a movement of the pumping section, the connecting elements hence acting for transferring the movement of the gear elements in a defined manner into a specified movement of the pumping section for causing a pumping action at the fluid conduit.

Each of the gear elements herein may be coupled to one of the connecting elements. A connecting element for example may be coupled to the associated gear element in a pivotable manner such that during rotation of the gear element the connecting element may pivot with respect to the gear element.

The connecting element specifically may be coupled to the associated gear element in an eccentric manner. In particular, each gear element may be rotatable about an associated rotational axis, the connecting element being coupled to the associated gear element at a coupling location eccentric to the rotational axis. When rotating the gear element, hence, the coupling location in an eccentric fashion rotates about the rotational axis, hence causing a planetary movement of the coupling location around the rotational axis and a corresponding movement of the connecting element. Such movement of the gear elements is transferred, via the connecting elements, to the pumping section, such that the pumping section is moved in a way such that fluid is forced to flow through the fluid conduit.

The coupling location of each gear element may be arranged in a predefined manner with respect to the coupling locations of other gear elements such that the pumping section is caused to move in a peristaltic fashion for forcing fluid through the fluid conduit. For example, the coupling location of a first gear element of the multiplicity of gear elements may be displaced along a first displacement direction from the rotational axis of the first gear element, whereas the coupling location of a second gear element of the multiplicity of gear elements is displaced along a second displacement direction from the rotational axis of the second gear element, the first displacement direction and the second displacement direction being angularly offset with respect to each other.

Beneficially, herein, the angular offset between the displacement directions of the first gear element and the second gear element remains constant during rotational movement of the gear elements.

In case neighbouring gear elements perform opposite rotational movements, no constant offset between the neighbouring gear elements exist. Herein, however, beneficially the displacement directions of a first gear element and a second gear element have a defined angular offset which are not directly neighbouring, but have one intermediary gear element placed therebetween. The first gear element and the second gear element rotate in equal rotational directions, whereas the intermediary gear element will rotate in an opposite rotational direction. In this case, hence, gear elements which are not directly neighbouring each other may have a predefined angular offset with respect to the coupling locations of their connecting elements.

In case neighbouring gear elements perform equal rotational movements and hence rotate in equal rotational directions, there beneficially is a constant angular offset between the displacement directions of the coupling locations of the connecting elements for the directly neighbouring gear elements.

By choosing a suitable angular offset with respect to the coupling locations for coupling the connecting elements to the gear elements, a suitable transfer of movement to the pumping section can be achieved, the movement of the pumping section being such that a peristaltic pump action at the pump section is obtained.

In one embodiment, the pumping section comprises a multiplicity of pumping elements, wherein neighbouring pumping elements of the multiplicity of pumping elements are pivotably coupled to each other at an associated pivot axis. The pumping section hence is formed by a chain of pumping elements pivotably coupled to each other, the pumping elements for example being formed by rigid beam sections forming a chain of pumping elements.

In this case each gear element may for example, by means of its associated connecting element, act onto a pivot axis in between neighbouring pumping elements, the gear elements beneficially acting onto different pairs of pumping elements such that each gear element acts onto the chain of pumping elements at a distinct pivot axis of a pair of neighbouring pumping elements. By rotational movement of the gear elements, hence, the chain of pumping elements can be moved in order to act onto the fluid conduit for forcing a fluid flow through the fluid conduit.

In another embodiment the pumping section may be formed by a flexibly deformable wall element, which beneficially may be integrally shaped and fabricated from an elastomeric material. The pumping section hence is formed as one piece, which may be flexibly deformed by movement of the gear elements, the gear elements for example being linked to the pumping section by means of connecting elements integrally connected to the pumping section.

The object is also achieved by means of a method for operating an infusion device for administering a medical fluid to a patient, the method comprising: acting, by means of a pumping mechanism, onto a fluid conduit, the pumping mechanism comprising a pumping section movable with respect to said fluid conduit for causing a fluid flow through said fluid conduit, and moving the pumping section using a multiplicity of rotatable gear elements of the pumping mechanism, wherein the rotatable gear elements are coupled to the pumping section at a multiplicity of different locations and are operatively coupled to each other such that the gear elements perform a coordinated rotation when moving the pumping section.

The advantages and advantageous embodiments described above for the infusion device equally apply also to the method, such that in this respect it shall be referred to the above.

The idea underlying the invention shall subsequently be described in more detail with reference to the embodiments shown in the figures. Herein:

FIG. 3 shows a schematic drawing of a pumping mechanism of an infusion device;

FIG. 4A to 4E show the pumping mechanism in different states during actuation for pumping a fluid through a fluid conduit;

FIG. 5 shows a schematic drawing of another embodiment of a pumping mechanism of an infusion device; and FIG. 6 shows a schematic drawing of angular offsets of coupling locations at which connecting elements are connected to gear elements of the pumping mechanism.

Figure 1:
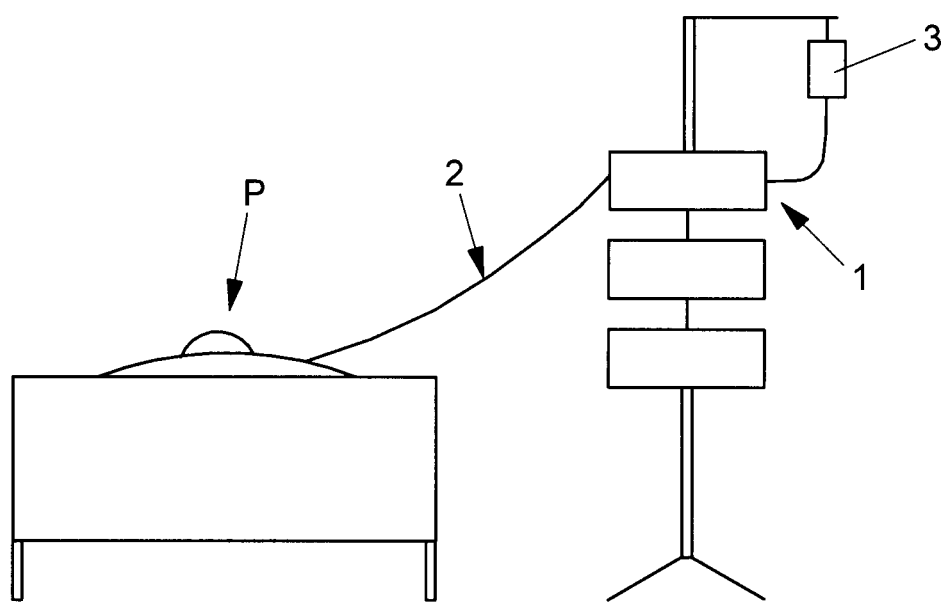
FIG. 1 shows a schematic drawing of an arrangement of infusion devices at the bedside of a patient.

Generally, as illustrated in FIG. 1, a multiplicity of infusion devices 1 may be arranged at the bedside of a patient P for delivering one or multiple medical fluids, such as medications, nutritional liquids, a saline solution or the like, to the patient P. The infusion devices 1 may be arranged on a stand and each serve to deliver a medical fluid from a container 3 via an infusion line 2 towards the patient P.

An infusion device 1 as concerned herein in particular is configured as a volumetric (peristaltic) infusion pump for performing a peristaltic pump action for transporting a fluid through an infusion line 2.

Figure 2:
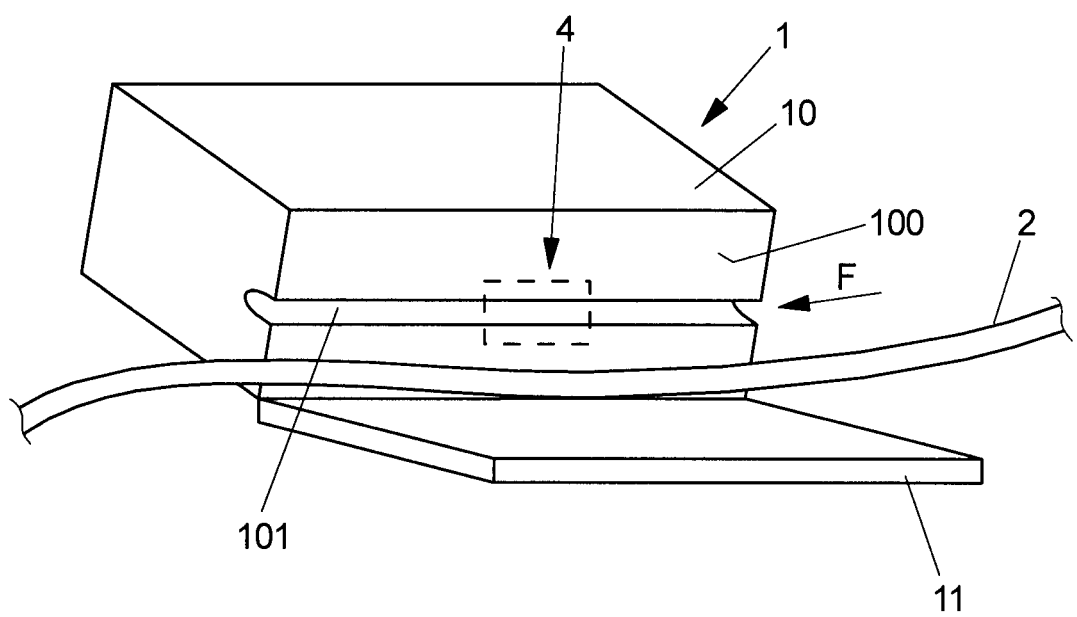
FIG. 2 shows a schematic drawing of an infusion device configured as a volumetric (peristaltic) infusion device.

As schematically shown in FIG. 2, an infusion device 1 of this type generally may comprise a housing 10 having a front face 100 on which a receptacle 101 for receiving an infusion line 2 is formed. A closure element 11 in the shape of a pivotable door may be connected to the housing 10 and may be closed in order to securely receive and fasten an infusion line 2 within the receptacle 101 formed on the front face 100 of the housing 10.

The infusion device 1 comprises a pumping mechanism 4 for acting onto the infusion line 2 or a pump module connected to the infusion line 2. The pumping mechanism 4 generally is configured to act onto the infusion line 2 in a peristaltic moving manner in order to force a fluid in a flow direction F through the fluid line 2 such that fluid is pumped through the infusion line 2 generally from a container 3 towards a patient P.

Different embodiments of such a pumping mechanism 4 are shown in FIGS. 3 to 5.

In one embodiment, as shown in FIG. 3, the pumping mechanism 4 comprises a multiplicity of gear elements 45A-45E in the shape of toothed wheels, each gear element 45A-45E being rotatable about an associated rotational axis 450 and carrying a toothing 452 on its circumferential outer face. The gear elements 45A-45E herein are in meshing engagement with each other in that a first gear element 45A meshes with a neighbouring, second gear element 45B, which additionally meshes with a neighbouring, third gear element 45C and so on. The gear elements 45A-45E hence are coupled to each other to form a gear train 45, the gear train 45 being such that the gear elements 45A-45E cannot be rotated independently of each other, but can be rotated only together in a coordinated fashion.

In the embodiment of FIG. 3, the first gear element 45A is linked to a drive device 46 for example in the shape of an electric drive motor, the first gear element 45A hence being driven, during operation, to rotate, hence causing the other gear elements 45B to 45E to rotate together with the first gear element 45A.

The gear elements 45A are rotatably mounted for example with respect to the housing 10.

The gear elements 45A-45E herein are coupled by means of corresponding connecting elements 44A-44E in the shape of rod elements to a pump section 42 formed by a multiplicity of pumping elements 420-425 in the shape of beam sections pivotably coupled to each other at pivot axes 43A-43E.

The connecting elements 44A-44E each, at a first end, are coupled to their associated, respective gear element 45A-45E at a coupling location 451, the coupling location 451 being eccentric to the respective rotational axis 450 of the gear element 45A-45E.

At a second end each connecting element 44A-44E is coupled to a pivot axis 43A-43E of a pair of neighbouring pumping elements 420-425.

The connecting elements 420-425 form a chain of beams pivotably coupled to each other. At one end 429 the chain of pumping elements 420-425 herein is pivotably coupled to a fixed wall section 41, for example a section of the housing 10. At a second end 426 the chain of pumping elements 420-425 is coupled to a coupling element 427 and via the coupling element 427 is pivotably coupled at a pivot axis 428 for example to the housing 10, the linkage at the end 426 allowing for a lateral adjustment movement at the end 426 during movement of the pumping section 42 in order to adjust for a lateral movement at the end 426 due to a change in shape of the pump section 42, as it will become apparent from FIGS. 4A to FIG. 4E.

The pumping section 42 serves to act onto a fluid conduit 20, which for example is formed by an infusion line 2 received within the receptacle 101 in between the housing 10 and the closure element 11 of the infusion device 1. The pumping section 42 herein, when moved by the gear elements 45A-45E, is in a periodic fashion pinched at moving locations, forcing in a peristaltic fashion a flow of fluid along a flow direction F through the fluid conduit 20.

Figure 4B:
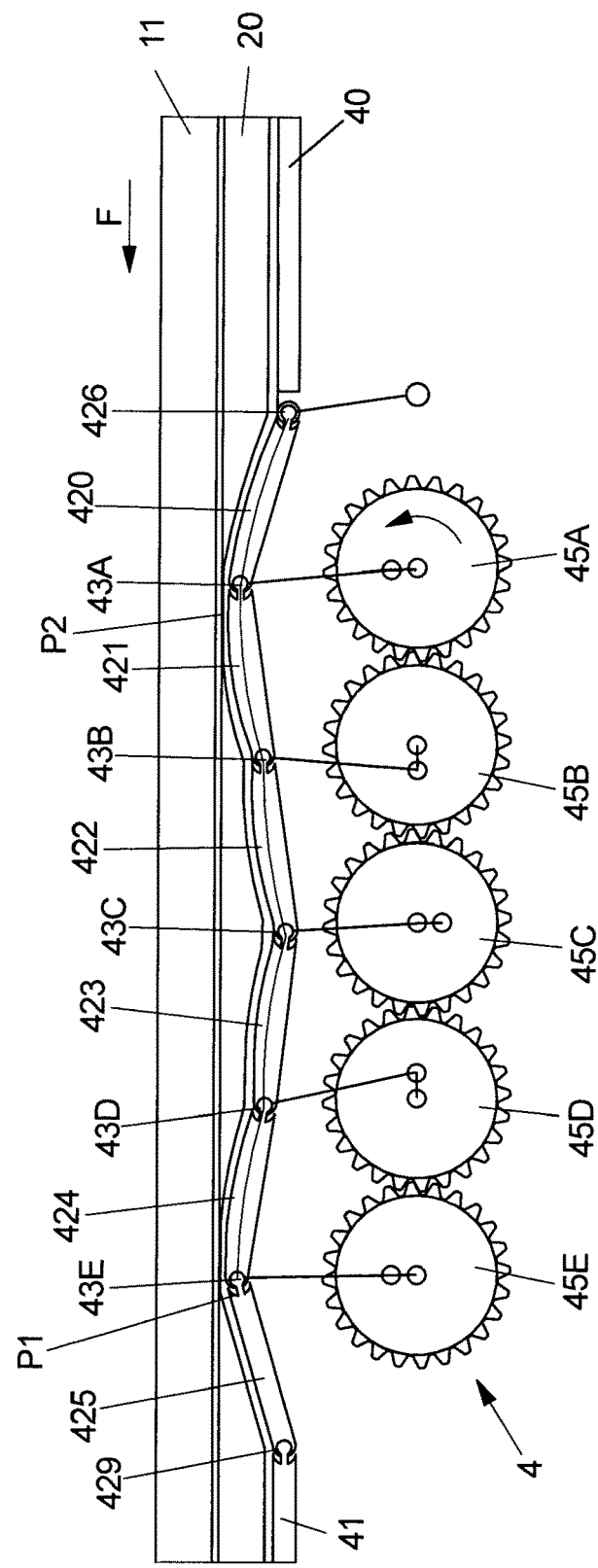

FIGS. 4A to FIG. 4E show the pumping mechanism 4 of FIG. 3 in different rotational states of the gear elements 45A-45E, denoted to states of 0°, 90°, 180°, 270° and 360°, the state of FIG. 4E hence matching the state of FIG. 4A, such that FIGS. 4A to 4E illustrate one complete revolution of the gear elements 45A-45E.

When driving the gear train 45 of the gear elements 45A-45E, the gear element 45A may for example be rotated, by means of an electric drive, in a counter clockwise rotational direction, as indicated in FIG. 3. This causes the neighbouring gear element 45B to rotate in a clockwise direction, the gear element 45C in a counterclockwise direction, the gear element 45D again in a clockwise direction, and the gear element 45E in a counterclockwise direction. During the rotational movement of the gear elements 45A-45E, herein, the coupling location 451 of each gear element 45A-45E eccentrically rotates about the rotational axis 450 of the associated gear element 45A-45E, such that the corresponding connecting element 44A-44E is moved eccentrically about the rotational axis 450 of the corresponding gear element 45A-45E.

When viewing FIGS. 4A to 4E, it can be observed that the pump section 42 causes locations of pinching P1, P2 at the fluid conduit 20, due to the movement of the gear elements 45A-45E, which move in the flow direction F and in this way force a fluid flow through the fluid conduit 20. In particular, when the coupling location 451 of a gear element 45A-45E is at a position pointing towards the fluid conduit 20, as it is the case in FIG. 4A for gear element 45D, the fluid conduit 20 will be pinched at a location of pinching P1 by the corresponding connecting element 44D. During rotational movement of the gear elements 45A-45E the location of depression P1, P2 moves in the flow direction F, as visible for the location of depression P1 in FIGS. 4A and 4B and for the location of depression P2 (following behind) in FIG. 4B to FIG. 4E. In this way, fluid is pushed through the fluid conduit 20, hence causing a fluid flow through the fluid conduit 20 in the flow direction F.

In the embodiment of FIG. 3 and FIGS. 4A to 4E neighbouring gear elements 45A-45E rotate in opposite rotational directions. The coupling locations 451 of the gear elements 45A-45E herein, as visible from FIG. 4A to FIG. 4E, are generally angularly offset with respect to each other, hence causing a peristaltic pumping action at the pump section 42.

As visible herein, gear elements 45A-45E rotating in the same rotational directions maintain their angular offset. For example, the gear elements 45A and 45C, at their coupling locations 451, have an offset of 180°, which is maintained during rotation of the gear elements 45A-45E, as visible from FIG. 4A to 4E.

This schematically is illustrated in FIG. 6. The coupling locations 451 at which the associated connecting element 44A-44E is coupled to the respective gear element 45A-45E is displaced with respect to the rotational axis 450 along a displacement direction X1-X5, the different displacement directions X1-X5 having generally an angular offset with respect to each other. The angular offset between the displacement directions X1-X5 between the gear elements 45A-45E rotating in the same rotational direction (for example gear elements 45A and 45C or gear elements 45B and 45D) herein remains constant during rotational movement of the gear elements 45A-45E.

As visible from FIG. 4A to 4E, the axial length of the chain of pumping elements 420-425 changes as the pumping elements 420-425 are moved by the gear elements 45A-45E. The change in axial length herein is adjusted by the coupling of the chain of pumping elements 420-425 at the end 426 by means of the coupling element 427, which is pivotably connected to the housing 10 at the pivot axis 428 and hence allows for an axial movement of the endpoint 26, as apparent for example from the transition from FIG. 4A to FIG. 4B.

In another embodiment illustrated in FIG. 5, the pumping mechanism 4 comprises a pumping section 42 formed by an integral wall element fabricated for example from an elastomeric material and hence being flexibly deformable. Connecting elements 44A-44E herein are integrally formed with the pumping section 42, the pumping section 42 being connected to fixed wall sections 40, 41 at its ends 426, 429.

As explained above according to the embodiment of FIGS. 3 and 4A to 4E gear elements 45A-45E are coupled to the pumping section 42 by means of the connecting elements 44A-44E. Herein, however the gear elements 45A-45E in the embodiment of FIG. 5 are coupled to each other to rotate in equal rotational directions in that between neighbouring gear elements 45A-45E in each case an intermediary tooth wheel 47 is arranged serving to couple neighbouring gear elements 45A-45E to each other. Each gear element 45A-45E herein meshes (dependent on its location in the gear train 45) with one or two of the tooth wheels 47, such that the gear elements 45A-45E are coupled to each other to rotate together when driving one of the gear elements 45A-45E by a drive device 46 for example in the shape of an electric motor.

In the embodiment of FIG. 5 the coupling locations 451 of the connecting elements 44A-44E at the gear elements 45A-45E are displaced in displacement directions which are angularly offset with respect to each other, as apparent from FIG. 5. Herein, because the gear elements 45A-45E are rotated in equal rotational directions the angular offset of neighbouring gear elements 45A-45E remains constant during rotational movement of the gear elements 45A-45E.

Other than that the principle peristaltic function of the embodiment of FIG. 5 is comparable to the function of the embodiment of FIGS. 3 and 4A to 4E, such that it shall in this respect be referred to the above.

The idea underlying the invention is not limited to the embodiments described above, but may be implemented also in an entirely different fashion.

An infusion device as described herein may be used to deliver different medical fluids, such as medication, nutritional liquid or the like, towards a patient.

The pumping mechanism of the infusion device herein may act onto an infusion line, or a pump module connected to an infusion line in order to exert a peristaltic pump action onto the infusion line.

LIST OF REFERENCE NUMERALS

1 Infusion device
10 Housing
100 Front face
101 Receptacle
11 Closure element
2 Infusion line
20 Fluid conduit
3 Container
4 Pump mechanism
40, 41 Fixed wall section
42 Deformable pumping section
420-425 Pumping element (beam section)
426 Coupling axis
427 Coupling element
428 Pivot axis
429 Pivot axis
43A-43E Location (pivot axis)
44A-44E Connecting element
45 Gear train
45A-45E Gear element
450 Rotational axis
451 Coupling location
452 Toothing
46 Drive motor
47 Tooth wheel
F Flow direction
P Patient
P1, P2 Locations of depression
X1-X5 Displacement direction

The invention claimed is:

1. An infusion device for administering a medical fluid to a patient, comprising:
a pumping mechanism configured to act onto a fluid conduit,
the pumping mechanism comprising a pumping section that abuts the fluid conduit and is movable with an undulating motion with respect to said fluid conduit as the pumping section abuts the fluid conduit for causing a fluid flow through said fluid conduit, a multiplicity of rotatable gear elements coupled to the pumping section at a multiplicity of different locations interconnected along the pumping section, and a multiplicity of connecting elements connecting the multiplicity of gear elements to the pumping section,
each connecting element being connected to the pumping section at one of the multiplicity of locations interconnected along the pumping section, each connecting element being formed by a rod element, wherein the gear elements are operatively coupled to each other for a coordinated rotation of the gear elements for moving the pumping section.

2. The infusion device according to claim 1, wherein the multiplicity of gear elements each comprise a toothing for operatively coupling the multiplicity of gear elements to each other.

3. The infusion device according to claim 1, wherein neighboring gear elements of the multiplicity of gear elements are operatively coupled to each other such that the neighboring gear elements are operative to rotate in opposite rotational directions.

4. The infusion device according to claim 1, wherein neighboring gear elements of the multiplicity of gear elements are operatively coupled to each other such that the neighboring gear elements are operative to rotate in a same rotational direction.

5. The infusion device according to claim 4, wherein a tooth wheel is arranged between neighboring gear elements of the multiplicity of gear elements for operatively coupling the neighboring gear elements to each other.

6. The infusion device according to claim 1, wherein each gear element of the multiplicity of gear elements is coupled to one connecting element of the multiplicity of connecting elements.

7. The infusion device according to claim 6, wherein each gear element of the multiplicity of gear elements is rotatable about an associated rotational axis, the one connecting element of the multiplicity of connecting elements being pivotally coupled to the associated gear element at a coupling location eccentric to the rotational axis.

8. The infusion device according to claim 1, wherein the pumping section comprises a multiplicity of pumping elements, wherein neighboring pumping elements of the multiplicity of pumping elements are pivotally coupled to each other at an associated pivot axis.

9. The infusion device according to claim 8, wherein each gear element of the multiplicity of gear elements is coupled to an associated pair of neighboring pumping elements at the pivot axis of the associated pair of neighboring pumping elements.

10. The infusion device according to claim 1, wherein the pumping section is formed by a flexibly deformable wall element.

11. An infusion device for administering a medical fluid to a patient, comprising:
a pumping mechanism configured to act onto a fluid conduit,
the pumping mechanism comprising a pumping section movable with respect to said fluid conduit for causing a fluid flow through said fluid conduit, a multiplicity of rotatable gear elements coupled to the pumping section at a multiplicity of different locations, and a multiplicity of connecting elements connecting the multiplicity of rotatable gear elements to the pumping section, each connecting element being connected to the pumping section at one of the multiplicity of different locations,
wherein the gear elements are operatively coupled to each other for a coordinated rotation of the gear elements for moving the pumping section
wherein each gear element of the multiplicity of gear elements is coupled to one connecting element of the multiplicity of connecting elements,
wherein each gear element of the multiplicity of gear elements is rotatable about an associated rotational axis, the one connecting element of the multiplicity of connecting elements being pivotally coupled to the associated gear element at a coupling location eccentric to the rotational axis, and
wherein the coupling location of a first gear element of the multiplicity of gear elements is displaced along a first displacement direction from the rotational axis of the first gear element, whereas the coupling location of a second gear element of the multiplicity of gear elements is displaced along a second displacement direction from the rotational axis of the second gear element, wherein the first displacement direction and the second displacement direction are angularly offset with respect to each other.

12. The infusion device according to claim 11, wherein the angular offset between the displacement directions of the first gear element and the second gear element remains constant during rotational movement of the multiplicity of gear elements.

13. A method for operating an infusion device for administering a medical fluid to a patient, comprising:
acting, by means of a pumping mechanism, onto a fluid conduit, the pumping mechanism comprising a pumping section that abuts the fluid conduit and is movable with an undulating motion with respect to said fluid conduit as the pumping section abuts the fluid conduit for causing a fluid flow through said fluid conduit, and
moving the pumping section using a multiplicity of rotatable gear elements of the pumping mechanism,
wherein the multiplicity of rotatable gear elements are coupled to the pumping section at a multiplicity of different locations interconnected along the pumping section with a multiplicity of connecting elements connecting the multiplicity of gear elements to the pumping section, each connecting element being connected to the pumping section at one of the multiplicity of locations interconnected along the pumping section, each connecting element being formed by a rod element, and
wherein the gear elements are operatively coupled to each other such that the multiplicity of gear elements perform a coordinated rotation when moving the pumping section.

* * * * *